(12) United States Patent
Kornek

(10) Patent No.: US 7,417,160 B2
(45) Date of Patent: Aug. 26, 2008

(54) METHOD FOR THE PRODUCTION OF SILICON COMPOUNDS CARRYING AMINO GROUPS

(75) Inventor: Thomas Kornek, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/382,332

(22) Filed: May 9, 2006

(65) Prior Publication Data

US 2006/0194976 A1    Aug. 31, 2006

Related U.S. Application Data

(63) Continuation of application No. PCT/EP2004/012805, filed on Nov. 11, 2004.

(30) Foreign Application Priority Data

Nov. 13, 2003  (DE)  ................................ 103 53 063

(51) Int. Cl.
  *C07F 7/10*  (2006.01)
(52) U.S. Cl. ..................................................... 556/424
(58) Field of Classification Search ........................ None
  See application file for complete search history.

(56) References Cited

U.S. PATENT DOCUMENTS

| | | | |
|---|---|---|---|
| 3,673,233 A | | 6/1972 | Golitz et al. |
| 4,555,561 A | | 11/1985 | Sugimori et al. |
| 5,446,181 A | * | 8/1995 | Uehara et al. ................ 556/424 |
| 2003/0130543 A1 | * | 7/2003 | Bauer et al. .................. 564/481 |
| 2004/0181025 A1 | | 9/2004 | Schindler et al. |

FOREIGN PATENT DOCUMENTS

| | | |
|---|---|---|
| DE | 1 812 564 | 6/1970 |
| DE | 195 13 976 A1 | 3/1996 |
| DE | 693 06 288 T2 | 4/1997 |
| DE | 199 41 283 A1 | 5/2000 |
| DE | 101 39 132 A1 | 2/2003 |
| EP | 0 702 017 A1 | 3/1996 |
| GB | 686068 | 1/1953 |

OTHER PUBLICATIONS

English Derwent Abstract Corresponding to EP 0 702 017 A1 [AN 1996-152656] [16].
English Derwent Abstract Corresponding to DE 195 13 976 A1 [AN 1996-152656] [16].
English Derwent Abstract Corresponding to DE 696 06 288 T2 [AN 1993-167014] [20].
English Derwent Abstract Corresponding to DE 199 41 283 A1 [AN 2000-444081] [39].

* cited by examiner

*Primary Examiner*—Samuel A Barts
(74) *Attorney, Agent, or Firm*—Brooks Kushman P.C.

(57) ABSTRACT

(N-organylaminoorganyl)triorganylsilanes and (N,N-diorganylamino-organyl)triorganyl silanes are prepared in exceptional yield and high purity by reacting a cyclic or acyclic amine with low water content with a haloorganylsilane.

8 Claims, No Drawings

METHOD FOR THE PRODUCTION OF SILICON COMPOUNDS CARRYING AMINO GROUPS

CROSS-REFERENCE TO RELATED APPLICATIONS

This application is a continuation of PCT application Ser. No. PCT/EP2004/012805, filed Nov. 11, 2004, to which priority is claimed, and which claims the benefit of German Application No. 103 53 063.0, filed Nov. 13, 2003, to which priority is also claimed.

BACKGROUND OF THE INVENTION

1. Field of the Invention

The invention relates to a method for the production of (N-organylaminoorganyl)- and (N,N-diorganylaminoorganyl)triorganylsilanes from corresponding (triorganylsilylorganyl) halides and N-organyl- or N, N-diorganylamines, and (N-cyclohexylaminomethyl)trimethoxysilane and [N,N-bis-(N',N'-dimethylaminopropyl)aminomethyl]triorganylsilane obtainable by means of this method.

2. Background Art (N-organylaminoorganyl)- and (N, N-diorganylamino-organyl)triorganylsilanes can be produced at present by means of three different methods.

Aminoalkyl-substituted silicon compounds having an alkylene bridge containing at least three C atoms positioned between the nitrogen and the silicon atom are obtained by hydrosilylation of corresponding unsaturated amine compounds with organosilicon compounds containing hydrogen atoms bonded to the silicon atom. Any free NH groups present on the amine-containing olefin component must be blocked by protective groups before the hydrosilylation reaction in order to avoid undesired secondary reactions.

Furthermore, (aminoorganyl)silanes can be converted into substituted (N-organylaminoorganyl)- and (N,N-diorganylaminoorganyl)triorganylsilanes by nucleophilic substitution reactions with the aid of organyl halides. A disadvantage of this method is the tendency of the organyl halides to undergo uncontrolled multiple alkylations.

The method for the production of (N-organylaminoorganyl)- and (N,N-diorganylaminoorganyl)triorganylsilanes by means of the reaction of (haloorganyl)silanes with corresponding amines is economically more advantageous than the two abovementioned methods. In particular, the ready availability of (chloroalkyl)silanes, which are obtainable by means of photochlorination of alkylsilanes or hydrosilylation of corresponding halogen-substituted olefins with Si-H-containing compounds, and are used, for example, as intermediates for the synthesis of a multiplicity of organofunctional silanes, proves to be advantageous. Furthermore, in this procedure, it is possible to employ a large number of similarly readily available primary and secondary amines for the synthesis of the (N-organylaminoorganyl)- and (N,N-diorganylaminoorganyl)triorganylsilanes which permits a very wide range of use of the method and therefore economical product changes with existing industrial production plants.

British patent GB 686,068 A discloses (amino)-, (N-organylamino)- and (N,N-diorganylaminomethyl)- or (N,N-diorganylaminoethyl)triorganylsilanes. Furthermore, GB 686,068 A also describes a method for reacting corresponding (chloromethyl)- or (bromomethyl)triorganosilanes with ammonia or a primary or secondary amine at temperatures of at least 50° C. for the production of (aminoorganyl)-, (N-organylaminoorganyl)- and (N,N-diorganylaminoorganyl)triorganylsilanes. As a rule, the (chloromethyl)- or (bromomethyl)triorganosilanes were initially introduced into a flask or autoclave, depending on the boiling points of the amine compounds used, and heated to temperatures above 100° C., particularly 110-130° C. In the case of higher-boiling amines, (e.g. cyclohexylamine) the sequence of mixing was the opposite and the (chloromethyl)- or (bromomethyl)triorganosilanes were added to the heated amine. The reaction time was from 2 to 8 hours depending on the amine compound to be reacted.

The (aminomethyl)silane derivatives are prepared by the method described in German Laid-open application DE 18 12 564 A1, by reacting a (chloromethyl)- or (bromomethyl)silane derivative with ammonia or a primary amine. The reaction is effected at temperatures of 80 to 100° C. for a period of 2 or 3 hours, the amine having been introduced initially in its entirety, in a molar excess of 1:3.2 to 1:6.

The methods described in GB 686,068 A and DE 18 12 564 A1 have very long reaction times, e.g. several hours. The yields obtained are low. The products are not obtained in the required purity and have to be purified by a complicated procedure before their further use. For example, the products obtained by the method described contain large amounts of ionogenic chloride or bromide. Without purification, their industrial use is limited. They cannot be used, for example, in sealing compounds which are applied to metallic surfaces, due to considerably greater corrosion due to the halides present.

In particular, the hydrochlorides or hydrobromides of the amines used in the synthesis, or the hydrochlorides or hydrobromides of the desired compounds are considered here as chloride- or bromide- containing impurities. In this context, it was surprisingly found that mixtures of (aminomethyl)silanes and the abovementioned hydrochlorides or hydrobromides can lead in some cases to very exothermic decomposition of the desired compounds with breaking of the Si—C bond and formation of correspondingly N-methylated amines at relatively high temperatures, as are necessary, for example, during the production and also for the distillative purification of the desired compounds. The N-methylamines thus formed influence the course of the synthesis in an undesired manner. This effect appears to correlate with the basicity of the amine compound: the less basic the (aminomethyl)silane, the more readily does this decomposition reaction occur. For this reason and also from the point of view of safety, low halide contents of the (aminomethyl)silanes described here are necessary. Although a number of methods for the reduction of halide contents in alkoxysilanes are known and are based, for example, on the precipitation of the dissolved halide by addition of alkali metal or alkaline earth metal alcoholate salts (e.g. EP 0 702 017 A1, DE 693 06 288 T2, DE 195 13 976 A1), superstoichiometric amounts of the salts are required for simple and efficient reduction of the halide content, since the desired complete removal of halide cannot be achieved by stoichiometric amounts. Disadvantageously, however, all (aminomethyl)silanes investigated to date tend under these conditions, such as the simultaneous presence of free alcohols and strong bases, to undergo decomposition reactions, for example, the breaking of the Si—C bond already described above. An alternative method which is said to permit reductions of chloride contents in alkoxysilanes by introduction of ammonia is described in German Laid-Open Application DE 199 41 283 A1, but here (aminoalkyl)alkoxysilanes are explicitly excluded from the field of use thereof. Furthermore, the heating of the completely premixed solution of silane and amine, described in DE 18 12 564 A1, is questionable from the point of view of plant safety owing to the exothermic reaction of the two components.

It has now been surprisingly discovered that the decomposition of (aminomethyl)silanes takes place not only in the presence of hydrochlorides, or of alcohols and bases, but the presence of alcohols alone is sufficient to bring about the formation of corresponding N-methylamines. The N-methylated amine derivatives thus formed compete during the reaction with unmethylated amine still present for reaction with the (halomethyl)silane and finally lead to the formation of (N-methylaminomethyl)silanes, which cannot be separated from the desired compounds by distillation. In order to avoid this undesired secondary reaction, alcohols must be absent from the reaction mixture. If at least one of the organyl radicals on the silicon atom is an alkoxy group, only amines having a low water content may be used in the method, since otherwise alcohols are liberated by preliminary reaction of the silane with water present in the amine.

SUMMARY OF THE INVENTION

It was therefore an object of the invention to eliminate the disadvantages of the existing methods for the production of (N-organylaminoorganyl)- and (N,N-diorganylaminoorganyl)triorganylsilanes of the prior art, and to provide a simple method which makes it possible to obtain (N-organylaminoorganyl)- and (N,N-diorganylaminoorganyl)triorganylsilanes in short reaction times in high yields and high purities. These and other objects were surprisingly achieved by a synthesis method in which the starting silane is initially introduced and heated and then the corresponding amine is added continuously. Furthermore, the halide contents in the desired compounds may be reduced by adding nonpolar solvents to the crude mixtures and separating off the precipitated salts. By using amines having a low water content, the liberation of alcohols during the synthesis, and hence the formation of byproducts is suppressed. Surprisingly, the amine or (aminomethyl)silane hydrohalide formed during the method can, if required, be removed from the mixture by double decomposition with ammonia, which furthermore prevents the formation of N-methylated byproducts. Although the teaching of the Laid-Open Application DE 199 41 283 A1 excludes this explicitly, it was surprisingly possible to obtain chloride-free (aminomethyl)silanes by passing ammonia into the crude or isolated end product.

DETAILED DESCRIPTION OF THE PREFERRED EMBODIMENT(S)

The invention therefore relates to a method for the production of (N-organylaminoorganyl)- and (N,N-diorganylaminoorganyl)triorganylsilanes of the general formula (1)

$$R_{3-n}R^1{}_n Si\!-\!R^2\!-\!NR^3R^4 \quad (1)$$

by reacting cyclic or acyclic amines having a low water content and of the general formula (2)

$$H\!-\!NR^3R^4, \quad (2)$$

whose water content is from 0 to 20,000 ppm, with (haloorganyl)silanes of the general formula (3)

$$R_{3-n}R^1{}_n Si\!-\!R^2\!-\!X \quad (3)$$

in which

R is a hydrocarbon or an alkoxy radical having 1-10 C atoms which may be saturated or unsaturated, branched or straight-chain, substituted or unsubstituted, $R^1$ is a hydrocarbon radical having 1-10 C atoms, which may be saturated or unsaturated, branched or straight-chain, substituted or unsubstituted, $R^2$ is a hydrocarbon diradical having 1-10 C atoms, which may be saturated or unsaturated, branched or straight-chain, substituted or unsubstituted, $R^3, R^4$ are hydrogen or a hydrocarbon radical having 1-10 C atoms, which may be saturated or unsaturated, branched or straight-chain, substituted or unsubstituted, with the proviso that $R^3, R^4$ may be identical or different and are optionally linked to one another, it also being possible for the resulting ring to contain heteroatoms, X is chlorine, bromine or iodine and n is a number equal to 1, 2 or 3.

The method comprises the following steps:

a) continuous addition of the (haloorganyl)silane of the general formula (3) over a period of from 1 to not more than 3 hours at a temperature of from 80° C. to 200° C., to a 3- to 6-fold excess of the amine of the general formula (2), which was initially introduced beforehand in the reaction space and heated to the reaction temperature, b) optional double decomposition of the resulting hydrohalides by introduction of ammonia during or after the addition of the (haloorganyl)silane, c) optional removal of the resulting ammonium salts after the end of the addition, d) removal of the excess amine after the end of the addition, e) optional addition of a nonpolar solvent for precipitation of still dissolved ammonium compounds with subsequent removal of the ammonium salts formed, f) optional addition of ammonia for precipitating still dissolved hydrohalides with subsequent removal of the ammonium salts formed, and g) optional distillation of the product.

The process can be operated continuously or batchwise.

The radicals $R^1$, $R^3$ and $R^4$, independently of one another, are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals, such as the cyclopentyl, cyclohexyl, cycloheptyl, and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as the o-, m- and p-tolyl radicals, xylyl radicals and ethylphenyl radicals; and aralkyl radicals, such as the benzyl radical and the α- and β-phenylethyl radicals; and combinations thereof linked by heteroatoms such as N, O, S, P. Preferably, not more than one of the radicals $R^3$ and $R^4$ is hydrogen. Furthermore, the radicals $R^3$ and $R^4$ may be linked directly or by heteroatoms, resulting in cyclic structures —$NR^3R^4$ with structural inclusion of the N atom. Examples of this are the morpholino, piperidino or pyrrolidino radicals, which are also preferred. The radical $NR^3R^4$ is also preferably the N,N-bis(N',N'-dimethylaminopropyl) radical.

$R^1$ is preferably a methyl, ethyl, isopropyl, n-propyl, isobutyl, n-butyl, pentyl, hexyl, heptyl, octyl, nonyl, decyl, phenyl, benzyl or allyl radical. The radicals $R^3$ and $R^4$ are preferably the same as $R^1$, or are furthermore cyclohexyl or phenyl radicals. In a particularly preferred embodiment, the radical $R^3$ is the phenyl or cyclohexyl radical and the radical $R^4$ is hydrogen.

The radical R has the meaning of $R^1$ or $OR^1$. R is preferably a methoxy, ethoxy, isopropoxy, n-propoxy, butoxy, phenoxy, benzyloxy or allyloxy radical.

The radical $R^2$ is preferably a methylene, ethylene, or propylene group, most preferably the methylene group.

The radical X may be chlorine, bromine or iodine, preferably chlorine or bromine, and most preferably, chlorine.

The subscript n is 0, 1, 2 or 3, preferably 1, 2 or 3.

Preferably, the water content of the amines of the general formula (2) which are to be used is from 0 to 20,000 ppm, preferably from 0 to 5,000 ppm, most preferably from 0 to 1,000 ppm.

With the inventive method, it was possible in a simple manner to obtain (N-organylaminoorganyl)- and (N,N-diorganylaminoorganyl)triorganylsilanes from corresponding (triorganylsilylorganyl) halides and N-organyl- or N,N-diorganylamines in quantitative yield.

The purity of the (N-organylaminoorganyl)- and (N,N-diorganylaminoorganyl)triorganylsilanes is at least 85%. This purity can be increased to above 95% by means of simple distillation.

Compared with the prior art, the inventive method has, in particular, the advantages that the reaction times can surprisingly be substantially shortened, for example to not more than 1 to 2 hours, with complete conversion still taking place in the reaction by suitable choice of reaction parameters such as process temperature. At the same time, the formation of byproducts is significantly reduced by the use of an excess of amine of the general formula (2), optionally by reducing the content of (aminomethyl)silane hydrohalide during the synthesis by double decomposition of the corresponding amine hydrohalides or (aminomethyl)silane hydrohalides to give ammonium halides by use of ammonia, and by the use of amines having a low water content in the mixture.

The addition of nonpolar, readily recyclable organic solvents before filtering off the ammonium salts formed during the reaction surprisingly proves to be very suitable for reducing or completely eliminating the content of ionogenic chloride, bromide or iodide in the product. This preferred embodiment furthermore leads, with an optional subsequent distillation of the products, to higher yields of the purified product. Furthermore, the entrainment of sublimable ammonium salts into the distillation plant is avoided. If, in a specific case, such measures do not result in complete removal of ionogenic chloride, bromide or iodide in the product, this aim can then be achieved by addition of ammonia and subsequent removal of the precipitate which separates out.

The invention furthermore relates to (N-cyclo-hexylaminomethyl)trimethoxysilane. (N-cyclohexylaminomethyl)trimethoxysilane (empirical formula $C_{10}H_{23}NO_3Si$, molar mass 233.38 g/mol) was obtained as a colorless liquid of alcoholic odor by the method according to the invention by reacting (chloromethyl)trimethoxysilane with cyclohexylamine.

The invention furthermore relates to [N,N-bis (N',N'-dimethyl-aminopropyl)aminomethyl]triorganylsilanes of the general formula (4)

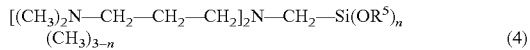

$$[(CH_3)_2N-CH_2-CH_2-CH_2]_2N-CH_2-Si(OR^5)_n \atop (CH_3)_{3-n} \qquad (4)$$

in which n is an integer 1, 2 or 3 and $R^5$ is the radical $-CH_2-CH_3$ or $CH_3$.

Thus, the invention relates to [N,N-bis(N',N'-dimethylaminopropyl)aminomethyl]triethoxysilane, [N,N-bis(N',N'-dimethylaminopropyl)aminomethyl]diethoxy(methyl)silane, [N,N-bis(N',N'-dimethylaminopropyl)aminomethyl] ethoxydimethylsilane, [N,N-bis(N',N'-dimethylaminopropyl)aminomethyl] trimethoxysilane, [N,N-bis(N',N'-dimethylaminopropyl)aminomethyl]dimethoxy(methyl)silane and [N,N-bis(N',N'-dimethylaminopropyl)aminomethyl] methoxydimethylsilane, which were obtained as colorless liquids having an alcoholic odor by the method according to the invention by reacting the silanes mentioned in table 1 with N,N-bis(N',N'-dimethylaminopropyl)amine.

TABLE 1

| Silane | Product | Empirical formula | Molar mass |
|---|---|---|---|
| $(EtO)_3Si(CH_2Cl)$ | [N,N-bis(N',N'-dimethylaminopropyl)aminomethyl]-triethoxysilane | $C_{17}H_{41}SiN_3O_3$ | 363.62 |
| $Me(EtO)_2Si(CH_2Cl)$ | [N,N-bis(N',N'-dimethylaminopropyl)aminomethyl]-diethoxy(methyl)silane | $C_{16}H_{39}SiN_3O_2$ | 333.59 |
| $Me_2(EtO)Si(CH_2Cl)$ | [N,N-bis(N',N'-dimethylaminopropyl)aminomethyl]-ethoxydimethylsilane | $C_{15}H_{37}SiN_3O$ | 303.57 |
| $(MeO)_3Si(CH_2Cl)$ | [N,N-bis(N',N'-dimethylaminopropyl)aminomethyl]-trimethoxysilane | $C_{14}H_{35}SiN_3O_3$ | 321.54 |
| $Me(MeO)_2Si(CH_2Cl)$ | [N,N-bis(N',N'-dimethylaminopropyl)aminomethyl]-dimethoxy(methyl)silane | $C_{14}H_{35}SiN_3O_2$ | 305.54 |
| $Me_2(MeO)Si(CH_2Cl)$ | [N,N-bis(N',N'-dimethylaminopropyl)aminomethyl]-methoxydimethylsilane | $C_{14}H_{35}SiN_3O$ | 289.54 |

(abbreviations: Me = $CH_3$; Et = $CH_2CH$)

All above symbols of the above formulae have their meaning in each case independently of one another.

In the following examples unless stated otherwise in each case, all stated amounts and percentages are based on weight and all pressure on 0.10 MPa (abs.).

EXAMPLE 1

Not According to the Invention

In a 500 ml three-necked flask having a reflux condenser, KPG stirrer and thermometer, 176 g of commercial cyclohexylamine (water content ≦2%) were heated to 100° C., and 122 g of (chloromethyl)ethoxydimethylsilane were added over the course of 30 min with stirring. After the end of the addition, the mixture was stirred for two hours under reflux and cooled to 30° C., and the white precipitate formed was filtered using a pressure filter, and rinsed with cyclohexylamine. Filtrate and wash solutions were combined and were freed from excess cyclohexylamine under reduced pressure. The subsequent fractional distillation gave 105 g (yield 61%) of (N-cyclohexylaminomethyl)ethoxydimethylsilane having a chloride content of 600 ppm.

EXAMPLE 2

In a 500 ml three-necked flask having a reflux condenser, KPG stirrer and thermometer, 317 g of dry cyclohexylamine were heated to 130° C., and 122 g of (chloromethyl)ethoxydimethylsilane were added in the course of 45 min with stirring. After the end of the addition, stirring was effected for a further 30 min at 130° C. and excess cyclohexylamine was distilled off under reduced pressure. Thereafter, the mixture was cooled to 30° C. and 150 ml of isohexane were added. Thereafter, the suspension was filtered using a pressure filter, and the precipitate was rinsed with two 80 ml portions of isohexane. Filtrate and wash solutions were combined and were freed from the solvent under reduced pressure. The subsequent fractional distillation gave 163 g (yield 95%) of (N-cyclohexyl-aminomethyl)ethoxydimethylsilane with a chloride content of <20 ppm. When 1% of ammonia was added before the distillation of the product and any precipitate which separated out was filtered off, a product having a chloride content of <10 ppm was obtained in the same yield.

EXAMPLE 3

Example 2 was repeated with the modification that 137 g of (chloromethyl)trimethoxysilane were used instead of 122 g of (chloromethyl)ethoxydimethylsilane. In the course of the fractional distillation, 176 g (yield 94%) of (N-cyclohexy-laminomethyl)trimethoxysilane having a chloride content of <20 ppm were obtained. When 1% of ammonia was added before the distillation of the product and any precipitate which had separated out was filtered off, a product having a chloride content of <10 ppm was obtained in the same yield.

EXAMPLE 4

In a 500 ml four-necked flask having a reflux condenser, KPG stirrer, thermometer and gas inlet tube, 298 g of dry aniline were heated to 130° C. and 124 g of (chloromethyl)methyldimethoxysilane were added over the course of 60 min with stirring. After the end of the addition, ammonia was passed through the mixture with stirring at constant temperature until no further reaction was observable (about 60 min). Thereafter, excess aniline was removed under reduced pressure, the suspension was cooled to 30° C. and then 150 ml of isohexane were added. Thereafter, the white precipitate formed was filtered using a pressure filter, and was rinsed with two 80 ml portions of isohexane. Filtrate and wash solutions were combined and were freed from the solvent under reduced pressure. The subsequent fractional distillation gave 160 g (yield 95%) of (N-phenylaminomethyl) dimethoxy(methyl)silane having a chloride content of <20 ppm. When 1% of ammonia was added before the distillation of the product and any precipitate which had separated out was filtered off, a product having a chloride content of <10 ppm was obtained in the same yield.

EXAMPLE 5

Example 4 was repeated with the modification that 137 g of (chloromethyl)trimethoxysilane were used instead of 124 g of (chloromethyl)methyldimethoxysilane. After working up by distillation, (N-phenyl-aminomethyl)trimethoxysilane was obtained in a yield of 94% and with a chloride content of <20 ppm. When 1% of ammonia was added before the distillation of the product and any precipitate which had separated out was filtered off, a product having a chloride content of <10 ppm was obtained in the same yield.

EXAMPLE 6

Example 4 was repeated with the modification that ammonia and silane were metered simultaneously into aniline and the mixture was then stirred for a further 30 min in an ammonia atmosphere at the stated temperature. The work-up was analogous to that of example 4, and gave 162 g (yield 96%) of (N-phenylaminomethyl)dimethoxy(methyl)silane having a chloride content of <20 ppm. When 1% of ammonia was added before the distillation of the product and any precipitate which had separated out was filtered off, a product having a chloride content of <10 ppm was obtained in the same yield.

EXAMPLE 7

Example 2 was repeated with the modification that 170 g of (chloromethyl)triethoxysilane were used instead of 122 g of (chloromethyl)ethoxydimethylsilane. In the course of the fractional distillation, 207 g (yield 94%) of (N-cyclohexy-laminomethyl)triethoxysilane having a chloride content of <20 ppm were obtained. When 1% of ammonia was added before the distillation of the product and any precipitate which had separated out was filtered off, a product having a chloride content of <10 ppm was obtained in the same yield.

EXAMPLE 8

Example 2 was repeated with the modification that 146 g of (chloromethyl)diethoxy(methyl)silane were used instead of 122 g of (chloromethyl)ethoxydimethylsilane. In the course of the fractional distillation, 186 g (yield 95%) of (N-cyclohexylaminomethyl)diethoxy(methyl)silane having a chloride content of <20 ppm were obtained. When 1% of ammonia was added before the distillation of the product and any precipitate which had separated out was filtered off, a product having a chloride content of <10 ppm was obtained in the same yield.

EXAMPLE 9

Example 7 was repeated with the modification that 279 g of dry morpholine were used instead of 317 g of dry cyclohexylamine. In the course of the fractional distillation, 204 g (yield 97%) of (N-morpholinomethyl)triethoxysilane having a chloride content of <20 ppm were obtained. When 1% of ammonia was added before the distillation of the product and any precipitate which separated out was filtered off, a product having a chloride content of <10 ppm was obtained in the same yield.

EXAMPLE 10

Example 8 was repeated with the modification that 599 g of dry N,N-bis(N',N'-dimethylaminopropyl)amine were used instead of 317 g of dry cyclohexylamine. In the course of the fractional distillation, 237 g (yield 89%) of [N,N-bis(N',N'-dimethylaminopropyl)aminomethyl]diethoxy(methyl)silane having a chloride content of <50 ppm were obtained. When 1% of ammonia was added before the distillation of the product and any precipitate which had separated out was filtered off, a product having a chloride content of <10 ppm was obtained in the same yield.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the production of (N-organylaminoorganyl)- and (N,N-diorganylaminoorganyl)triorganylsilanes of the formula (1)

by reacting cyclic or acyclic amines of the formula (2)

whose water content is from 0 to 20,000 ppm,
with (haloorganyl)silanes of the formula (3)

in which
R are a $C_{1-10}$ hydrocarbon or $C_{1-10}$ alkoxy radicals which are saturated or unsaturated, branched or straight-chain, substituted or unsubstituted,
$R^1$ is a $C_{1-10}$ hydrocarbon radical which is saturated or unsaturated, branched or straight-chain, substituted or unsubstituted,
$R^2$ is a $C_{1-10}$ hydrocarbon radical which is saturated or unsaturated, branched or straight-chain, substituted or unsubstituted,
$R^3$, $R^4$ are hydrogen or a $C_{1-10}$ hydrocarbon radical which is saturated or unsaturated, branched or straight-chain, substituted or unsubstituted, wherein $R^3$, $R^4$ are identical or different and are optionally linked to one another to form a ring structure optionally containing one or more heteroatoms, and at least one of $R^3$ and $R^4$ is not hydrogen,
X is chlorine, bromine or iodine and
n is a number equal to 1, 2 or 3,
the process comprising the steps of
a) continuously adding (haloorganyl)silane of formula (3) over a period of from 1 to not more than 3 hours at a temperature of from 80° C. to 200° C., to a 3- to 6-fold stoichiometric excess of amine of the formula (2), which was initially present and heated to the reaction temperature,
b) introducing ammonia during or after the addition of the (haloorganyl)silane to commence double decomposition of hydrohalides,
c) removing of ammonium salts formed in step b) after the end of the addition, and
d) removing excess amine after the end of the addition.

2. The process of claim 1, further comprising, following step d),
e) adding a nonpolar solvent to precipitate dissolved ammonium compounds and subsequently removing the ammonium salts formed.

3. The process of claim 1, further comprising:
f) adding ammonia to precipitate dissolved hydrohalides and subsequently removing ammonium salts formed thereby.

4. The process of claim 1, further comprising:
g) distilling the product of formula (1).

5. The process of claim 1, wherein the water content of the amines of formula (2) does not exceed 1000 ppm.

6. The process of claim 2, wherein nonpolar, readily recyclable organic solvents are used in step e).

7. The process of claim 1, wherein independently of one another the radicals $R^3$ and $R^4$ are selected from the group consisting of cyclohexyl, phenyl and hydrogen, or $R^3$ and $R^4$ are linked directly or by one or more heteroatoms, resulting in cyclic structures —$NR^3R^4$ with structural inclusion of the N atom.

8. The process of claim 7, wherein that the cyclic structure —$NR^3R^4$ is a morpholino, piperidino or pyrrolidino radical.

* * * * *